United States Patent [19]
Schuster

[11] 4,016,806
[45] Apr. 12, 1977

[54] METHOD AND APPARATUS FOR MAKING TRANSVERSE CLOSURE SEALS IN COMPOSITE THERMOPLASTIC BAG STOCK

[76] Inventor: Samuel J. Schuster, 617 Vallombrosa, Pasadena, Calif. 91107

[22] Filed: Apr. 5, 1976

[21] Appl. No.: 673,916

[52] U.S. Cl. .................................. 93/35 R; 93/14; 93/33 H
[51] Int. Cl.² .......................................... B31B 1/84
[58] Field of Search .......... 93/8 R, 14, 33 H, 35 R, 93/DIG. 1; 156/583

[56] References Cited
UNITED STATES PATENTS 3,837,972  9/1974  Schuster ............................ 156/583

Primary Examiner—Gerald A. Dost
Attorney, Agent, or Firm—Fraser and Bogucki

[57] ABSTRACT

High integrity transverse closure seals are made in thermoplastic, tubular bag stock by the application of a first, low temperature seal to one face of the bag stock followed by the application of a second, low temperature seal to the other face, in substantial registration with the first seal, to finalize the closure seal.

One of the seals is wider than the other and the narrower seal is positioned within the confines of the wider seal.

17 Claims, 6 Drawing Figures

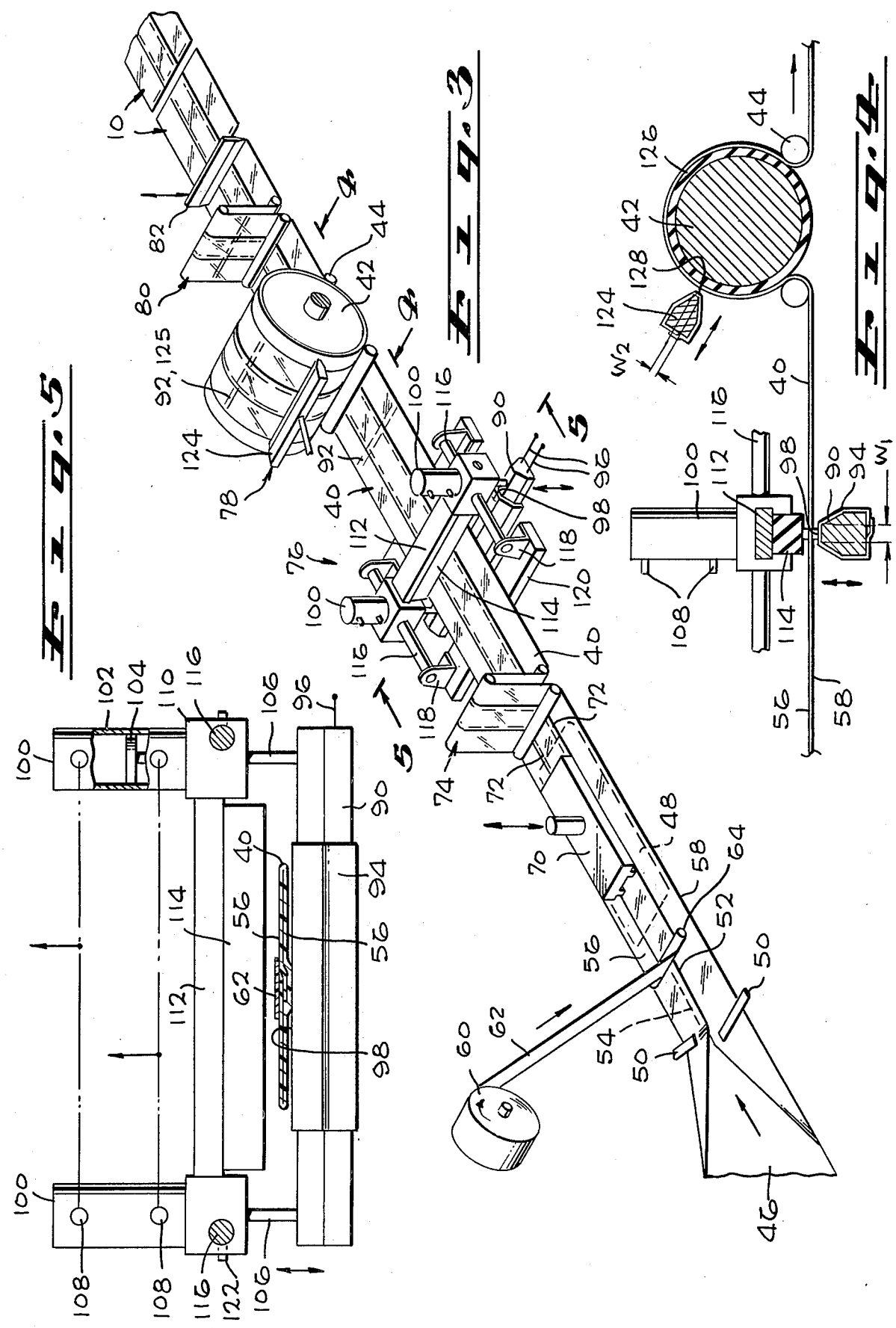

METHOD AND APPARATUS FOR MAKING TRANSVERSE CLOSURE SEALS IN COMPOSITE THERMOPLASTIC BAG STOCK

BACKGROUND OF THE INVENTION

The present invention relates to a method and apparatus for producing high integrity transverse closure heat seals in tubular thermoplastic bag stock and is particularly applicable to making such closure seals in bag stock having transverse cross-sectional properties which make difficult the application of such transverse closure seals without melting, singeing or otherwise degrading the bag stock.

The invention finds its primary use in the fabrication of flexible, thermoplastic, vapor-sterilizable bags for storing articles in bacteria-free condition such as those shown in U.S. Pat. Nos. 3,472,369 and 3,761,013 issued to the present inventor on Oct. 14, 1969 and Sept. 25, 1973, respectively.

Such containers are formed from a continuous sheet of polyethylene, polypropylene, or the like, the side margins of which are folded inwardly along longitudinal fold lines. The margins, which typically are in overlapping relationship, define a longitudinal access opening. A closure membrane or tear strip of paper of "Tyvek" (a spun polyolefin of the duPont Company), for example, covers the access opening and is bonded to the folded sheet by a longitudinally-extending heat seal on each side of the opening. The ends of the bag are closed by transverse heat seals joining the various plies of plastic sheet and the tear strip.

The transverse closure heat seals must be of high integrity, that is, they must be completely impervious to the passage of bacteria. Such transverse heat seals are generally applied by a single heat seal bar brought into contact with the front or upper face of the bag stock, that is, the face to which the tear strip is attached, as the bag stock passes about a feed drum having a resilient outer surface which functions as a back-up surface for the transverse heat seal bar.

It will be evident that the above-described bags, viewed in transverse cross-section, have thicknesses and material compositions that vary along the transverse section, ranging from two plies of plastic sheet along the outer margins of the bag to four plies, consisting of three plies of plastic and the single ply tear strip, in the central portion. Such differential thicknesses and composition make the application of a transverse heat seal of the required high integrity difficult. If the transverse seal bar is heated to a temperature sufficient to assure adequate sealing of the central, thicker portion of the bag within a reasonably short dwell period, singeing, melting, burnthroughs or other degradation of the bag stock material adjacent the heat seal bar frequently occurs. This is especially a problem with "Tyvek" which deteriorates rapidly when exposed to excessive temperatures.

The foregoing problems are also particularly evident in the fabrication of gusseted bags, that is, bags provided with reentrant folds, and heavy-walled bags with sheet thicknesses ranging, for example, from 6 to 8 mils.

In the foregoing instances, the transverse heat seal bar temperatures of 450°–600° F. typically in use today result in excessive numbers of rejected bags. As another consequence, the anti-stick coverings such as "Teflon" (trademark of the duPont Company for plastic consisting of a tetrafluoroethylene polymer) over the heat seal bars tend to rapidly deteriorate at these temperatures and thus must be replaced quite frequently.

Attempts have been made to overcome the aforementioned problems by lowering the temperature of the transverse heat seal bar. However, this requires a concomitant increase in the dwell period and for this reason has not been successful in preventing the formation of seals of inadequate integrity. Production rates are also decreased, of course, as a result of the increase in dwell.

Another approach to solving the foregoing problems has been to maintain the surface of the feed drum at an elevated temperature to decrease the temperature gradient across the thickness of the bag stock so that the heat seal bar can be maintained at a substantially lower temperature. However, it has been found that the bag stock not only has a tendency to stick to the heated drum surface but coherence of the entire front and back faces of the bag stock takes place as well.

The application of the transverse closure heat seal by a pair of opposed heat seal bars operated to simultaneously clamp the bag stock between them has also been attempted. However, even when heated to only moderate temperatures such seal bars tend to excessively soften the plastic and special tension control and cooling apparatus is required to prevent the bag stock from being pulled apart at the seal. Moreover, with this technique the alignment and temperature of the sealing bars is critical and because a resilient back-up surface cannot be used, the uniformity of the gauge, composition and other physical properties of the bag stock must be carefully controlled.

SUMMARY OF THE INVENTION

Broadly, the present invention overcomes the above-described problems by dividing the process of producing the transverse closure heat seal between two sealing stations spaced apart along the bag stock feed path and cooperating with the opposed faces of the bag stock. By making the transverse closure seal in two stages, with the first sealing operation being applied to one of the faces and the second sealing operation being applied to the other face, substantially lower heat sealer temperatures may be used thereby preventing degradation of the bag stock while obtaining increased production rates by decreasing the dwell time required to perform each sealing operation.

More particularly, at the first sealing station a low temperature heat seal bar is applied to one of the faces of the tubular bag stock to effect at least a partial or preliminary seal. At the second sealing station a second low temperature heat seal bar is applied to the other face in substantial registration with the preliminary seal and before the preliminary seal has completely cooled, to complete the transverse heat seal. The second heat seal operation is preferably applied to the upper face of the bag stock, that is, the face including the tear strip, against the resilient feed drum.

In accordance with another aspect of the invention, the first or preliminary seal has a width greater than the second or final seal and the second seal is positioned within the confines of the first seal. These width and positional relationships assure the proper registration of the first and second seals and allow for some stretching or contraction of the bag stock between sealing stations. Also, because the impression left by each heat seal bar is visible, the correct positional relationship of the seals may be easily verified by visual inspection.

The two stage sealing technique of the invention allows the temperature of both heat seal bars to be reduced to about 200° F. for processing typical bag stock comprising, for example, 3 mil polyethylene and 7–10 mil "Tyvek", while maintaining a dwell of about 0.5 second. The dwell period can be halved and the production rate doubled by raising the temperature of the heat seals to 300° F., still well below the temperatures currently being used.

The sealing stations are separated along the bag stock feed path by a distance equal to an integral number of bag lengths. Preferably, the separation distance is one bag length so that the area to which the preliminary sealing operation has been applied has not cooled excessively by the time it arrives at the second sealing station.

BRIEF DESCRIPTION OF THE DRAWINGS

Further objects, advantages and features of the present invention will become clear from the ensuing detailed description of the preferred embodiment when read in conjunction with the accompanying drawings, in which:

FIG. 3 is a perspective view, somewhat schematic in nature, of a bag-making apparatus incorporating features of the present invention;

FIG. 4 is a side view, partly in cross section, of a portion of the apparatus of FIG. 3 as seen along the line 4—4;

FIG. 5 is a transverse cross-section view of the apparatus of FIG. 3 as seen along the line 5—5.

DETAILED DESCRIPTION OF THE PREFERRED EMBODIMENT

At the outset, it is to be noted that in the accompanying drawings the thicknesses of the plastic sheet and tear strip material have been exaggerated to more clearly show their interrelationship. Further, in the description that follows the term "longitudinal" denotes directions generally parallel with the direction of the feed path of the bag-making apparatus and the term "transverse" denotes directions generally perpendicular to the longitudinal direction.

Figure 1:
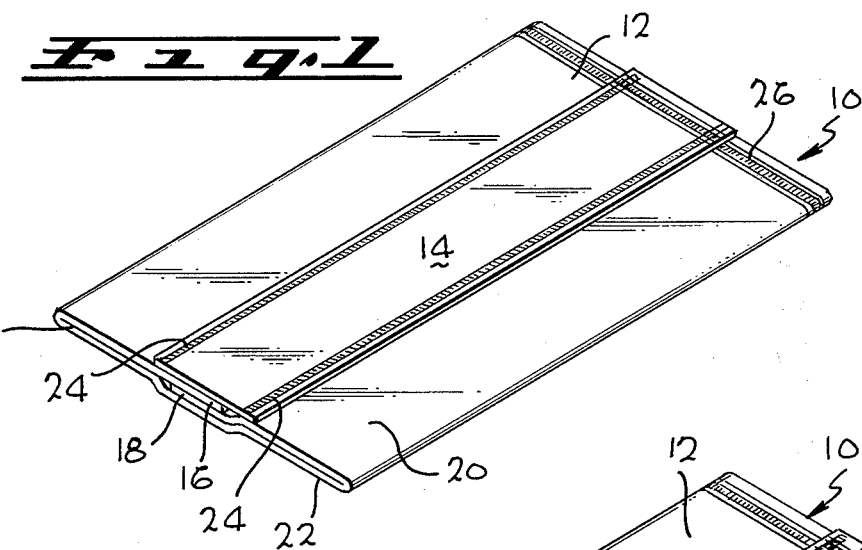
FIGS. 1 and 2 are perspective views of examples of bags having transverse closure seals made in accordance with the present invention.

Referring now to FIG. 1, there is shown a bag 10 exemplifying the type of bag structure to which the present invention has particular relevance. The bag 10 comprises generally a main portion 12 of heat sealable plastic sheet essentially completely impermeable to bacteria and a removable closure membrane or tear strip 14 of a material, such as paper or "Tyvek" that is also essentially completely impermeable to bacteria but highly permeable, in comparison to the plastic sheet, to sterilizing vapor such as steam or ethylene oxide. The bag further has longitudinally-extending edge margins 16 and 18 in overlapping relationship to define a longitudinal access opening covered by the closure membrane 14 and through which an enclosed sterilized article is adapted to be withdrawn following removal or pulling back of the tear strip 14. Reference may be made to the above-mentioned U.S. Pat. Nos. 3,472,369 and 3,761,013 for further descriptions of the structural features and use of such bags.

By way of arbitrary definition, the face of the bag including the tear strip 14 will be designated the upper face 20 while the opposite face will be designated the lower face 22.

The tear strip 14 is bonded to the upper face of the bag by longitudinal heat seals 24 while one end of the bag is sealed by a transverse closure heat seal 26. It is the making of this transverse heat seal that is the subject of the present invention.

The transverse end 28 of the bag opposite the sealed end is open to receive the article to be stored. Following insertion of the article, the open end is sealed with an appropriate transverse seal applied either manually or as a secondary operation on a "form and fill" machine combining the bag fabrication, filling and sealing functions.

Figure 2:
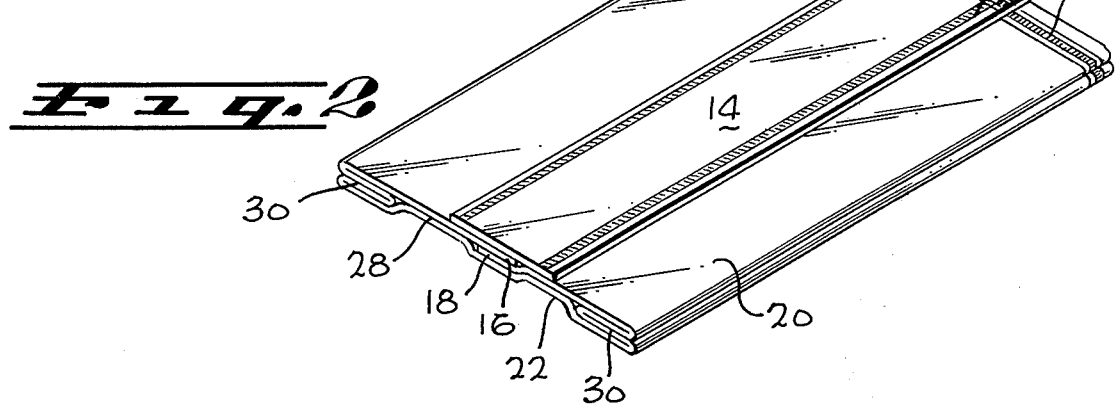

FIG. 2 shows a bag 10a identical in all respects to that shown in FIG. 1 except that the side portions have reentrant folds 30. It will be seen that the bags of FIGS. 1 and 2 have thicknesses and material compositions that vary substantially along their transverse cross sections.

FIGS. 3–5 show an apparatus for providing high integrity transverse closure seals such as the seals 26 in the bags shown in FIGS. 1 and 2. It will be appreciated by those skilled in the art, however, that the apparatus and method of the present invention may be used advantageously in connection with virtually any thermoplastic bag stock structure presenting sealing problems such as described earlier. For example, the invention may be used to make high integrity transverse closure seals in bag stock having a substantially uniform but thick transverse cross section resulting from the use of heavy gauge single or multiple ply plastic sheet.

The apparatus of FIGS. 3–5 fabricates bags 10 from bag stock 40 advanced intermittently a distance of one bag length along a feed path defined generally by the various operating stations of the apparatus. The bag stock 40 is advanced by an intermittently rotatable feed drum 42 that coacts with a feed roller 44 biased toward the drum 42. The feed drum 42 is actuated by an appropriate drive unit (not shown) whose structure and operation are well known in the art. During the dwell period between successive advancements of the bag stock 40, the various fabrication operations, including the application of the heat seals are performed.

The bag stock 40 is made from a continuous web or sheet 46 of polyethylene, polypropylene, nylon, polybutylene, or the like, drawn from a suitable supply roll (not shown) and maintained under the required tension in a well-known manner. As it advances, the sheet 46 is folded about a plate mandrel 48 by the action of forming fingers 50. The sheet 46 is thus formed into a continuous tube with the longitudinal edge margins 52, 54 of the sheet being disposed in overlapping relationship. The tube thus envelopes the plate mandrel 48 which is interposed between the upper and lower faces 56 and 58, respectively, of the tube.

The closure membrane or tear strip is fed from a supply roll 60 as a continuous strip 62 around a roller 64 and into contact with the upper face 56 of the folded plastic sheet to cover the overlapping margins 52, 54. The folded plastic sheet 46 and strip 62 together form the tubular bag stock 40 which is eventually cut into individual bags 10.

During each dwell period between successive feeds of the bag stock a longitudinally-oriented heat sealer 70 is operated to join the tear strip 62 and the upper face 56 of the plastic tube by means of a heat seal 72 applied along each side of the overlapping margins.

From the longitudinal heat sealer 70 the tubular bag stock 40 passes about a first compensator mechanism 74, past a first transverse heat seal station 76 and then around the feed drum 42.

A second transverse heat seal station 78 is located along the feed drum. During each dwell period the transverse heat seal stations 76 and 78 are operated to apply preliminary and final transverse heat seals as will be described in greater detail below.

The position of the seals applied by the longitudinal heat sealer 70 relative to the transverse heat seal is controlled by the first compensator mechanism 74 the structure and operation of which is well known.

After leaving the feed drum 42, the tubular bag stock 40 is threaded through a second compensator mechanism 80, identical to the first compensator mechanism 74, following which the bag stock is separated into individual bags 10 by a mechanical or thermal cutter 82 operable during each dwell period. The second compensator mechanism 80 is adjusted to precisely determine the position of the cut made by the cutter 82 relative to the transverse closure heat seal.

Figure 6:
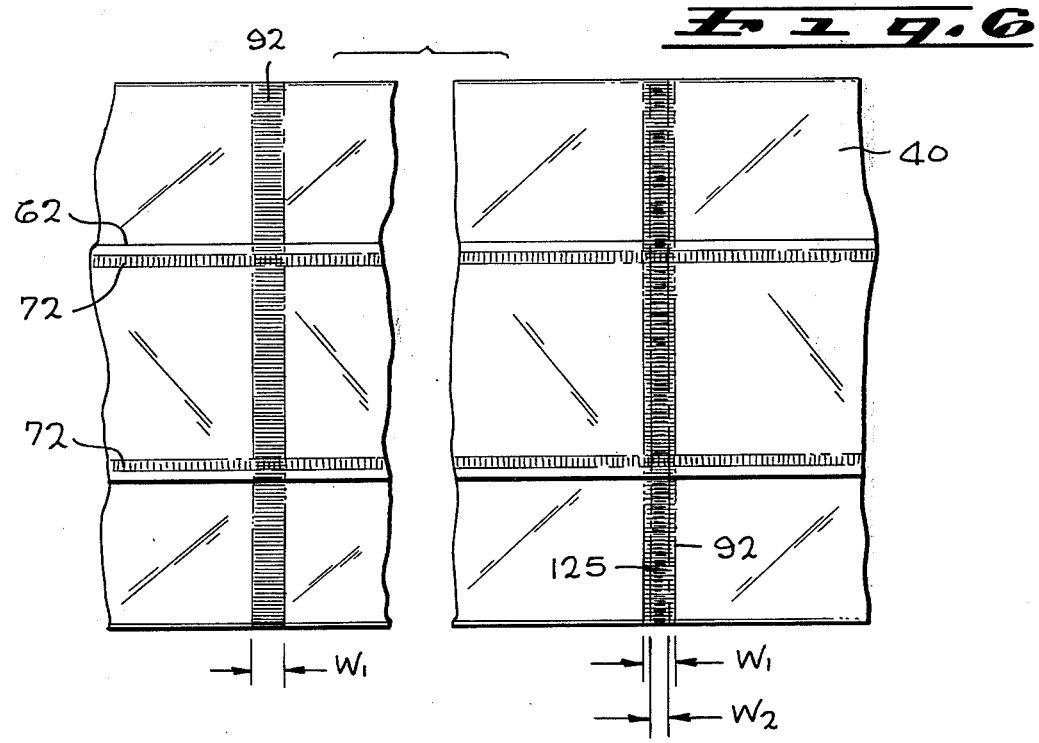
FIG. 6 is a top view of portions of bag stock processed by the apparatus of FIG. 3 illustrating transverse seals applied in accordance with the invention.

With reference now also to FIG. 6, the first transverse heat sealing station 76 includes a heat seal bar 90 operable in timed relation with the motion of the bag stock 40 to provide at least a partial or preliminary transverse seal 92 during each dwell period. The seal 92 is applied by the bar 90 against the lower face 58 of the bag stock. The heat seal bar 90 is enveloped in a "Teflon" or other anti-stick covering 94 and is typically maintained at a temperature of about 200°–300° F. by an electrical heating coil whose input leads are shown at 96. The horizontal sealing face 98 of the bar 90 has a width $w_1$, as best shown in FIG. 4.

The heat seal bar 90 is reciprocated by a pair of pneumatic actuators 100 including cylinders 102, pistons 104 and connecting rods 106 coupled to the ends of the bar 90. Each cylinder 102 has a pair of ports 108 connected in parallel to a suitable air pressure source via solenoid valves energized by microswitches controlled by appropriately shaped cam means connected to the main feed drum drive. The phenumatic actuators 100 thereby reciprocate the heat seal bar in timed relation with the intermittent advancement of the bag stock. Details of the pneumatic actuating system have been omitted for the sake of clarity and because they comprise well-known expedients in the art.

The cylinders 102 are mounted on blocks 110 connected by a plate 112 supporting a transversely oriented, resilient backup pad 114 in vertical alignment with the heat seal bar 90. The blocks 110 are mounted on longitudinally-extending dowels 116 which in turn are secured by brackets 118 to the machine frame, portions of which are shown at 120. It will be appreciated that the entire assembly comprising the pneumatic actuators 100, blocks 110, plate 112, backup pad 114 and heat seal bar 90 is movable longitudinally as a unit along the dowels 116 to obtain the appropriate positional relationsip between the first and second transverse seals. Once the correct position of the heat seal bar assembly has been ascertained for a given production run, the blocks 110 are firmly secured to the dowels 116 by set screws 122.

The second heat seal station 78 includes a transversely extending heat seal bar 124 suitably mounted (by means not shown but well known in the art) to reciprocate into and out of engagement with the upper face 56 of the bag stock to apply the second or final seal 125. The heat seal bar 124 presses the bag stock 40 against the feed drum which has a resilient outer surface 126. The sealing face 128 of the heat seal bar 124 has a width $w_2$ that in the embodiment under discussion is narrower than $w_1$. Like the heat seal bar 90, the bar 124 is also maintained at a low temperature of about 200°–300° F., well below the temperature at which melting, singeing or other degradation of the bag stock typically occurs.

The position of the heat seal assembly of the first sealing station 76 is adjusted along the dowels 116 so that the narrow seal 125 falls within the confines of the wider seal 92 as best shown in FIG. 6. In accordance with one practical example of the invention, $w_1$ is about ⅜inches and $w_2$ is about ⅛inches. These width relationships, of course, can be reversed. Although seals of equal widths may be employed (that is, where $w_1 = w_2$), this is not as desirable because if the overlap between them is small an excessive amount of bag length is taken up by the seal. More important, however, it would be left up to the discretion of the machine operator to determine if the amount of overlap is sufficient, an obviously undesirable decision-making process in the context of the production rates that are required in the industry. By using different seal widths as described it is immediately apparent whether or not the narrow seal is within the confines of the wider seal because the narrow seal is clearly visible against the wider seal. The dimensions of the seal widths are chosen so that allowance is made for the small amount of bag stock stretching or contraction that is typically experienced, consistent with maintaining the smallest overall seal width.

The invention, besides eliminating the described degradation of the bag stock material, allows higher production rates to be achieved. For example, by raising the temperatures of the heat seal bars to about 300° F., still well below the temperature at which degradation typically occurs, the dwell period may be substantially reduced with a concomitant increase in bag stock speed.

The distance along the feed path between the first and second heat seal bars is an integral number of bag lengths so that the appropriate registration of the seals is attained. Preferably, however that distance is one bag length so that when the second seal is applied the temperature of the area of the bag stock affected by the first seal will still be sufficiently elevated so that the temperature gradient across the thickness of the bag remains substantially reduced thereby facilitating the application of the second seal. As a further result thereof, in certain instances the temperature of the second heat seal bar may be maintained at a somewhat lower temperature than the first heat seal bar.

What is claimed is:

1. Apparatus for making high integrity, transverse closure heat seals in continuous, tubular thermoplastic bag stock of diverse transverse cross-section thickness and/or composition, the bag stock having opposed faces, the apparatus comprising:
    means defining a feed path for guiding the bag stock;
    a first low temperature, transverse heat seal bar disposed along the feed path for applying heat to one of the faces of the stock to at least partially seal the bag stock, said first heat seal bar adapted to coact with an opposed resilient back-up surface;

a second low temperature, transverse heat seal bar spaced apart from the first heat seal bar and disposed along the feed path for applying heat to the other face of the bag stock along a transversely-extending area at least partially coinciding with the seal applied by the first heat seal bar first to complete the transverse closure seal, the second heat seal bar adapted to coact with an opposed, resilient back-up surface;

means for intermittently advancing the bag stock in a direction from the first heat seal bar towards the second heat seal bar along the feed path between dwell periods;

means operatively associated with the bag stock advancing means for reciprocating the first heat seal bar toward and away from the feed path in timed relation with the intermittent advancement of the bag stock to effect the first seal during dwell periods; and means operatively associated with the bag stock advancing means for reciprocating the second heat seal bar toward and away from the feed path in timed relation with the intermittent advancement of the bag stock to effect the second seal during dwell periods.

2. The invention, as set forth in claim 1, in which the second heat seal bar is disposed an integral number of bag lengths from the first heat seal bar.

3. The invention, as set forth in claim 1, in which one of the heat seal bars is wider than the other, the narrower seal being positioned within the bounds of the wider seal.

4. The invention, as set forth in claim 1, in which the advancing means comprises a rotatable drum having a resilient outer surface, and in which the second heat seal bar coacts with the outer surface of the drum.

5. The invention, as set forth in claim 1, in which the first heat seal bar is adjustably positionable along the feed path to preset the positional relationship between the seals applied by the first and second heat seal bars.

6. A method of making high integrity, transverse closure seals in continuous, flattened, tubular bag stock of thermoplastic material, the bag stock having opposed faces, comprising the steps of:
advancing the bag stock;
stopping the advance of the bag stock for a dwell period;
applying heat during the dwell period at a first sealing station to one of the faces along a first area extendng transverse of the length of the bag stock to at least partially fuse the bag stock;
advancing the bag stock;
stopping the advance of the bag stock for a dwell period when said fused area of said stock arrives at a second sealing station; and
applying heat during the dwell period at the second station to the other face along a second transverse area in substantial registration with the first-mentioned area to finalize the closure seal.

7. The method of claim 6, wherein the second seal area is narrower than, and is positioned within the bounds of, the first seal area.

8. Apparatus for making bags from thermoplastic bag stock comprising tubular plastic sheet having juxtaposed edge margins and a closure strip covering the edge margins, said bag stock having an upper face including said strip and a lower face, said apparatus including:

means for intermittently advancing the bag stock one bag length along a longitudinally-extending feed path, said advancing means being operable to interpose a dwell period between successive advancements of said bag stock;

a longitudinal heat sealer disposed along said feed path and adapted to join said upper face of said bag stock to said strip by a longitudinal heat seal extending parallel to said edge margins, said longitudinal heat sealer being operable in timed relation with said advancing means to apply said longitudinal heat seals during each dwell period;

a first transverse heat sealing station disposed along said feed path a predetermined distance from said longitudinal heat sealer, said first transverse heat sealing station being operable in timed relation with said advancing means and including a low temperature transverse heat seal bar operatively associated with said feed path to apply at least a partial transverse closure seal to one of the faces of said bag stock during each dwell period;

a second transverse heat sealing station disposed along said feed path approximately an integral number of bag lengths from said first transverse heat sealing station, said second heat sealing station being operable in timed relation with said advancing means and including a low temperature transverse heat seal bar operatively associated with said feed path to apply during each dwell period a final transverse closure seal to the other of said faces of said bag stock in at least substantial registration with the first-mentioned seal; and means operatively associated with said feed path for separating said bag stock into individual bag lengths, said separating means being operable in timed relation with said advancing means to separate said bag stock adjacent said transverse closure heat seal.

9. Apparatus, as defined in claim 8, in which:
said advancing means comprises an intermittently rotatable feed drum having a resilient outer surface, said heat seal bar of said second heat sealing station applying said final heat seal to said upper face of said bag stock while said bag stock is in engagement with said feed drum, said resilient outer surface comprising a back-up surface for said final heat seal bar.

10. Apparatus, as defined in claim 8, in which:
the heat seal applied by one of said first and second heat seal stations is wider than the heat seal applied by the other of said stations, the narrower seal being positioned within the confines of the wider seal.

11. Apparatus, as defined in claim 10, in which:
the wider heat seal is applied by the first heat seal station.

12. Apparatus, as defined in claim 8, in which:
the distance between said first and second heat seal stations is approximately one bag length.

13. Apparatus, as defined in claim 8, in which:
the heat seal bar of said first heat seal station is adjustably positionable along said feed path to preset the distance between said first and second heat seal stations.

14. A method of making bags from thermoplastic bag stock comprising tubular plastic sheet having juxtaposed, longitudinally-extending edge margins and a longitudinally-extending closure strip covering the edge margins, said bag stock having an upper face including said strip and an opposed lower face, said method comprising the steps of:

heat sealing said closure strip to said upper face with a longitudinally-extending heat seal along each side of said juxtaposed edge margins;

advancing said bag stock;

stopping said bag stock for a dwell period;

applying a first low temperature transverse heat seal to one of the bag stock faces across the entire width of said bag stock and intersecting said longitudinal seals to at least partially seal together said upper and lower faces and said strip;

advancing said bag stock a predetermined distance;

stopping said bag stock for a dwell period;

applying a second low temperature transverse heat seal to the other of the bag stock faces across the entire width of said bag stock and in substantial registration with said first transverse heat seal;

advancing said bag stock a predetermined distance; and cutting said bag stock into individual bags adjacent said transverse heat seals.

15. The method, as defined in claim 14, in which:
said first transverse heat seal is applied to the upper face.

16. The method, as defined in claim 14, in which:
one of said transverse heat seals is wider than the other, the narrower seal being positioned within the confines of the wider seal.

17. The method, as defined in claim 16, in which:
said first transverse heat seal is wider than the second transverse heat seal.

* * * * *